United States Patent [19] [11] 4,215,679

Rustin [45] Aug. 5, 1980

[54] CIRCULATION ASSIST DEVICE FOR BODY EXTREMITIES

[76] Inventor: Jesse L. Rustin, Rte. 2, Dahlonega, Ga. 30533

[21] Appl. No.: 940,035

[22] Filed: Sep. 6, 1978

[51] Int. Cl.[2] .............................................. A61M 1/02

[52] U.S. Cl. .................................. 128/25 B; 272/129; 128/DIG. 20

[58] Field of Search .................... 128/30.2, 64, 61, 44, 128/52, 24 R, 24.1, 24.2, 25 R, 25 B, 66, 60, 400, 401, 402, 204, DIG. 20; 272/129, DIG. 5, DIG. 6

[56] References Cited

U.S. PATENT DOCUMENTS

| | | | |
|---|---|---|---|
| 2,265,729 | 12/1941 | Hall | 128/52 |
| 3,292,613 | 12/1966 | MacLeod | 128/40 |
| 3,396,721 | 8/1968 | Mencacci | 128/64 |
| 3,859,989 | 1/1975 | Spielberg | 128/24 R |

FOREIGN PATENT DOCUMENTS

| | | | |
|---|---|---|---|
| 2106508 | 9/1971 | Fed. Rep. of Germany | 128/64 |
| 368861 | 5/1973 | U.S.S.R. | 128/24 R |
| 395090 | 8/1973 | U.S.S.R. | 128/204 |

*Primary Examiner*—Robert W. Michell
*Assistant Examiner*—J. L. Kruter
*Attorney, Agent, or Firm*—Clarence A. O'Brien; Harvey B. Jacobson

[57] ABSTRACT

The device comprises modular parts with one module being an airtight casing shaped to approximate the shape of the limb needing circulation assistance. A pressure module may be attached to the end of the casing. This module includes a diaphragm which is operated by control circuitry responsive to a first sensor positioned to provide an indication of the entry of a blood pulse to the extremity. This sensor provides a timing pulse which activates a solenoid attached to the diaphragm. The timing pulse is passed through a variable time delay which time delay is controlled by a second sensor connected at a point on the extremity. The second sensor provides an indication of the amplitude of the blood pulse which passes through the extremity. The time delay period is varied to provide maximum amplitude of the pulse blood flow within the extremity. Furthermore, an exercise module may be connected to the casing in order to provide the patient with a means for actively stimulating his own blood circulation. The exerciser comprises a plunger having four positions into which it may be placed to activate one of four switches. Upon activation of each switch, an indicator dial position within sight of the patient will advance. The patient is instructed to activate each switch sequentially in order to move the indicator dial clockwise about the indicator face. Furthermore, a device is included in order to provide a means for applying pressure to an open wound existing in the extremity in order to bring opposing surfaces of the wound into contact and thereby encourage healing of the wound.

10 Claims, 11 Drawing Figures

CIRCULATION ASSIST DEVICE FOR BODY EXTREMITIES

BACKGROUND OF THE INVENTION

1. Field of the Invention

This invention relates to devices used for promoting blood circulation in body extremities and in particular to such devices which provide automatic means for enhancing blood circulation as well as a means to provide active participation of the patient.

2. Description of the Prior Art

Circulation devices shown in the prior art include U.S. Pat. No. 2,168,611, issued Aug. 8, 1939 to Thompson, which discloses a method of subjecting a plurality of parts of the human body to the changes of absolute pressure. The method comprises continuously moving gas into and out of two or more separate chambers such that a super atmospheric pressure is maintained in one chamber while a vacuum is maintained in one or more of the other chambers. U.S. Pat. No. 2,781,041, issued Feb. 12, 1957 to Weinberg, shows an apparatus for the progressive compression of body extremities. The apparatus comprises a sleeve for enclosing a human extremity made up of pressure applying cells positioned in end-to-end relation and an inner inflatable cell within and embracing the longitudinal extent of the first named cells and means for succcessive inflating the first cells and then the longer inner cell. U.S. Pat. No. 3,094,983, issued June 25, 1963, to MacLeod, shows a circulation assist device comprising a chamber for accepting a body extremity, the chamber having a seal for connection to the body extremity at one end and means for filling the chamber with liquid and means for varying the pressure of the liquid in the chamber. U.S. Pat. No. 3,783,859, issued Jan. 8, 1974, to Sauer et al, shows a circulatory assist device which utilizes the movement of a shell portion of a limb enclosing housing as a mechanical means for applying a requisite cyclic pressure to the limbs of a patient being treated. U.S. Pat. No. 3,865,103, issued Feb. 11, 1975, to Folman, shows a blood circulating device having a pair of airtight sleeves for encasing a body extremity, a slow air release valve in each of the sleeves and a source of compressed air connected to each sleeve at a point spaced from the valve for pulsatingly supplying air to each sleeve. U.S. Pat. No. 3,866,604, issued Feb. 18, 1975, to Curless et al, discloses a cardiac assist device which comprises a plurality of gas fillable bladders which are wrapped about a human limb and means for selectively inflating and deflating the bladders by the admission of gas into and withdrawal of gas from the bladders. U.S. Pat. No. 3,878, 839, issued Apr. 22, 1975, to Norton et al, shows a cardiac assist apparatus comprising a rigid housing having a pair of hingedly connected portions pivotally mounted relative to each other, means for clamping the portions together and a closed pneumatic pressure actuation means within the housing which provides pressure to the body extremity in synchronism with the patient's heart beat.

SUMMARY OF THE INVENTION

An object of the present invention is to provide a circulation assist device for body extremities which increases and decreases pressure in the vicinity of the body extremity in order to enhance the blood circulation therethrough.

A further object of the present invention is to provide a blood circulation device for body extremities wherein the increase and decrease of the pressure which induces the circulation of blood is synchronized with the pulsating blood entering the extremity and automatically adjusted to produce maximum blood flow.

A still further object of the present invention is to provide a circulation assist device wherein the patient may be provided with a means to actively participate in providing his own extremity with enhanced blood circulation.

Yet one still further object of the present invention is to provide a blood circulation assist device wherein the device may be made economically by providing component portions which may be easily attached to one another as needed.

Yet one still further object of the present invention is to provide a circulation assist device which has incorporated therein an apparatus for covering and providing pressure to any open wound existing in the limb being aided by the circulation assist device.

Yet one still further object of the present invention is to provide a device whereby a patient may monitor his own progress in increasing blood flow in an injuried extremity.

Accordingly, in keeping with the objects of the present invention as set forth hereinabove, the device comprises a casing composed of two symmetrical portions hinged longitudinally to each other. The casing is provided with an airtight seal at one end through which the extremity is inserted thus exposing the extremity in an airtight chamber. Within the chamber there is located a diaphragm attached to a solenoid device. The diaphragm is operative to increase and decrease the pressure in the chamber in order to provide circulation assistance to the extremity. Also located within the device is an exerciser which is designed to provide the patient with a means to exercise the extremity and thus enhance the circulation therein. Externally of the casing is a control system which monitors the patient's heart beat, a blood surge prior to the injured extremity and a blood surge at the distal point of the extremity from the heart and controls actuation of the diaphragm solemoid in order to provide pressurization to the extremity in synchronism with the natural flow of blood therethrough.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
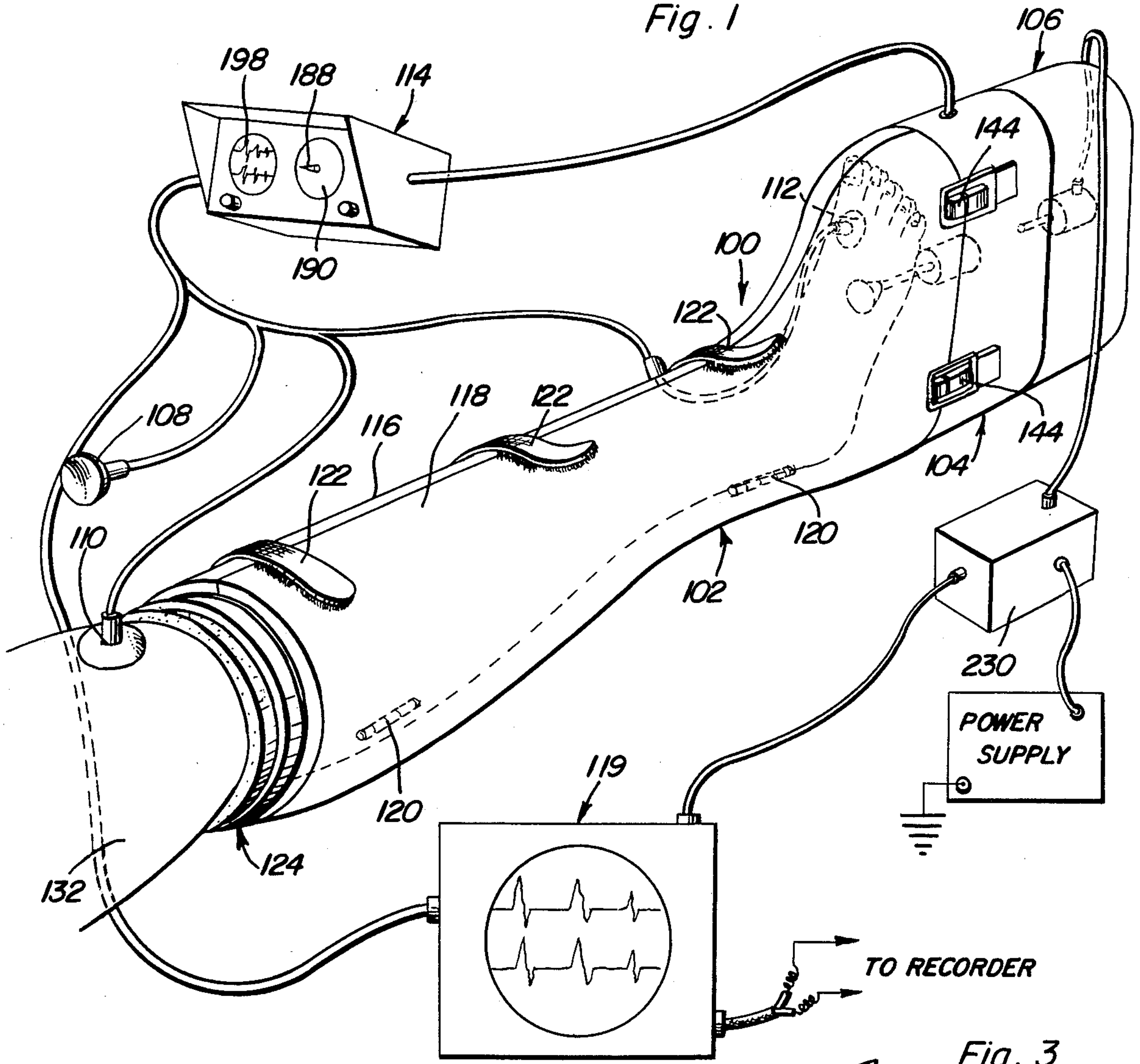
FIG. 1 is a prespective view of the circulation assist device of the present invention as used upon a patient's leg.

The circulation assist device will now be thoroughly described with reference to the drawings wherein the device itself is generally referred to by the numeral 100. The device includes leg casing module 102, exercise module 104, and pressurization module 106. The device also includes heart beat sensor 108, initial extremity surge sensor 110, and distal extremity surge sensor 112. Each of these sensors may be standard pressure sensitive devices which produce electrical pulses having an amplitude proportional to the pressure produced by the surge of blood through an artery. Each of the sensors are connected to patient monitoring station 114 and controls 119.

Figure 2:
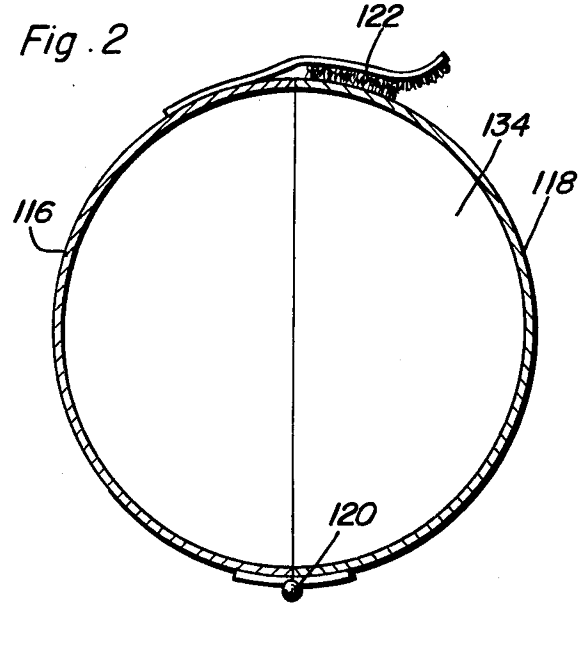
FIG. 2 is a sectional view of the casing of the circulation assist device.
Figure 7:
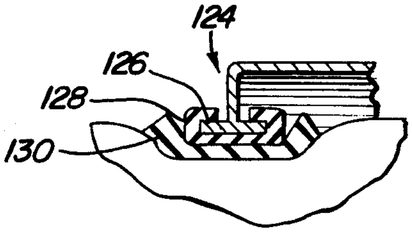
FIG. 7 is an enlarged sectional view of the sealing arrangement of the circulation assist device.

Leg casing module 102 can be seen most clearly with reference to FIGS. 1, 2 and 7, This module comprises two symmetrical shell portions 116 and 118 which are connected by a pair of hinges 120 on the bottom and held firmly in place by straps 122 which may employ a fastening means such as Velcro in order to alow for a firm secure engagement of the two shell portions. The shell portions when formed into the casing should take on the shape of the extremity being assisted. Shown in the drawings, is the leg of a patient about which the casing module is formed. It should be noted that the device is not limited to application only to use with a leg, the device may be formed to fit any other body extremity as well.

Figure 10:
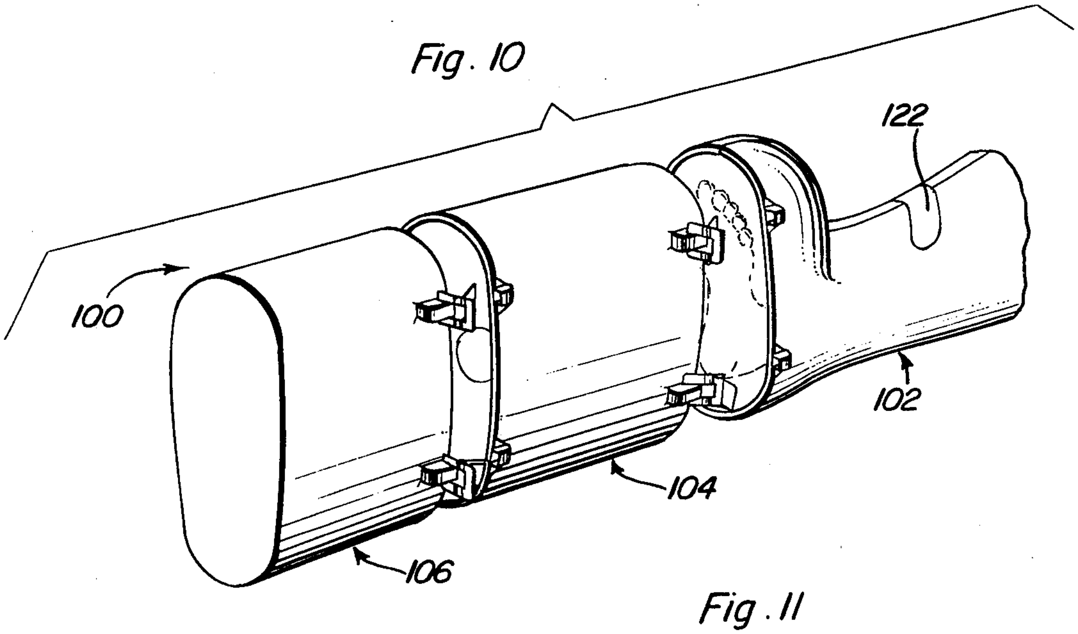
FIG. 10 is an exploded view showing the component nature of the circulation assist device.

A limb seal shown generally at 124 and in detail in FIG. 7 is connected to the open end of leg casing module 102 in order to provide an airtight seal between the shell portions and the extremity. Limb seal 124 comprises two semi-circular flanges 126 with one flange being formed in the end of each of the shell portions so as to form a continuous annual flange about the open end of the limb casing module. Disposed upon the flanges is a continuous styrofoam covering 128. This styrofoam covering provides a non-slip surface against which a large plastic pad 130 is disposed. The plastic pad forms a pressure seal between the styrofoam covering and the patient's leg shown at 132. This seal together with any suitable sealing means which runs along the joining edges of the symmetrical shell portions serve to define an airtight chamber 134 in which the patient's leg is disposed. The opposite end of the limb casing is open as seen in FIG. 10, for acceptance of the next module to be attached thereto. An airtight seal between modules must also be maintained for proper operation of the device. The symmetrical shells themselves may be made of rigid plastic or any other suitable hard material.

Figure 3:
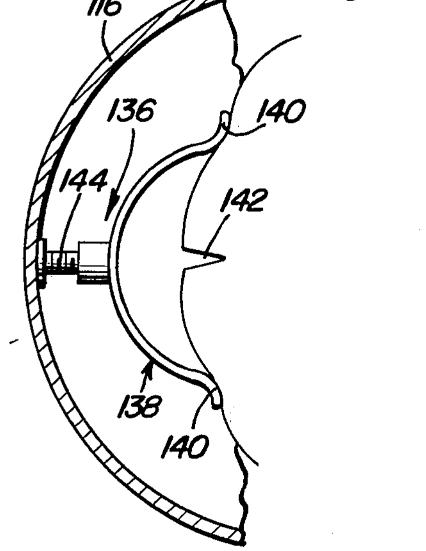
FIG. 3 is a part sectional view of the device showing the wound covering apparatus.

Mounted within the chamber 134 may be wound pressurizing apparatus shown generally at 136 in FIG. 3. Apparatus 136 comprises a generally U-shaped band of spring steel or other suitable, flexible material. Band 138 has recurved ends 140 which are placed on either side of wound 142 in order to apply laterally inward pressure on the wound. The band may be adjusted by screwing it in or out on stud 144 which is mounted for this purpose on the interior of one of the shells, in this case shell 116.

Figure 4:
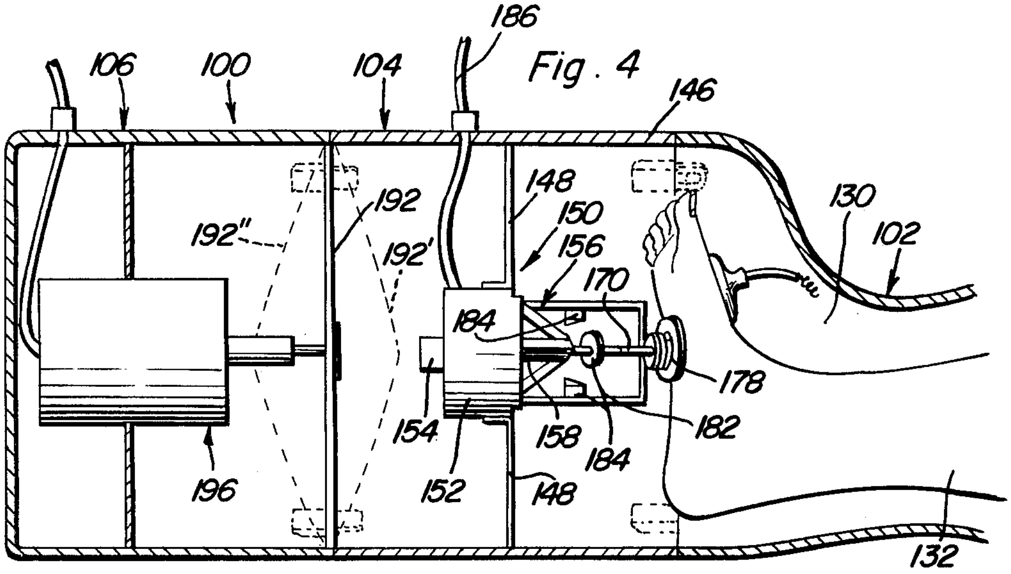
FIG. 4 is a elevational part sectional view of the device showing the interior components thereof.
Figure 5:
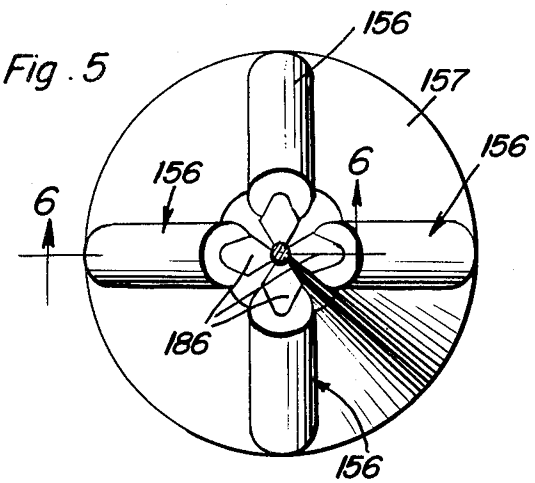
FIG. 5 is a frontal view of the exercise apparatus of the device.
Figure 6:
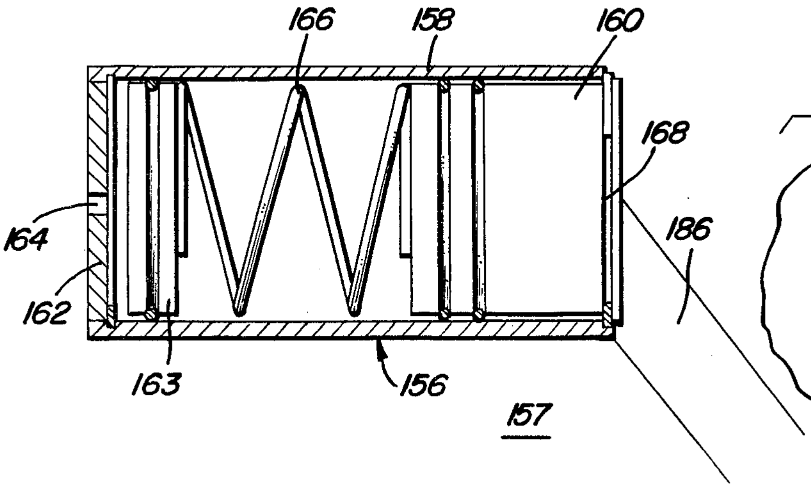
FIG. 6 is an elevational part sectional view of one cylinder of the exercise apparatus.
Figure 9:
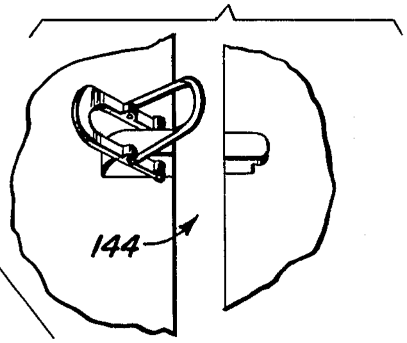
FIG. 9 is a detailed view of the latch used for connecting the components of the device.

Exercise module 104 as shown in FIGS. 1, 4 and 10 is attached to the open end of limb casing module 102 by clasps 144 provided for this purpose and shown clearly in FIG. 9. Again, an airtight seal must be maintained at the point of contact of these modules. Exercise module 104 includes casing 146 which includes, supported therein by support rods 148, an exercising apparatus 150. Exercising apparatus 150 consists of hydraulic reservoir 152 which contains hydraulic fluid. Expansion relief cylinder 154, which is essentially a spring loaded piston against which the hydraulic fluid of the reservoir may act, is attached to the rear of the hydraulic reservoir. With reference to FIGS. 4 and 5, it will be seen that forward of the hydraulic reservoir 152 are mounted four exercise cylinders 156. The cylinders are mounted upon a conical member 157 which has depressions provided therein for accepting each cylinder. Each piston consists of a cylindrical housing 158 shown in FIG. 6, a piston 160 mounted within the cylinder for axial movement therein, a base 162 having an aperture 164 disposed therein for hydraulic communication with the reservoir 152, and a return spring 166 which is biased at one end against the plate 163 and at the other end against piston 160. Piston 160 also has a depression 168 located centrally therein for accepting a wobble stick 170 as will be discussed hereinafter. It can be seen that upon movement of piston 160 axially within the cylinder 156, hydraulic fluid in the cylinder is forced through aperture 164 into reservoir 152 and expanlease cylinder 154. Cylinder 154 is configured similarly to each cylinder 156 except that fluid may be forced through an aperture and against a piston wherein such fluid movement is opposed by a spring similar to that shown at 166. It can be seen then that the force necessary to move piston 160 axially within cylinder 156 is dependent upon the force of spring 166, the diameter of piston 160 in the dimensions of like elements in piston 154. This construction will afford resistance relative to pressure and can be used by weak or strong persons with equal ease.

Figure 8:
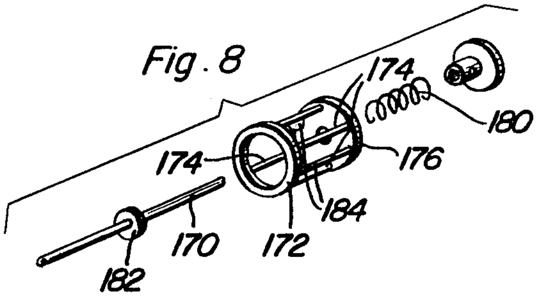
FIG. 8 is an exploded view of the wobble stick support of the exercise apparatus.

The four pistons 160 are depressed one at a time in sequential order by the use of a wobble stick 170 shown in FIGS. 4 and 8. The wobble stick is mounted for pivotal movement by a mounting unit which consists of an annular ring 172 which is connected to reservoir 152, and four laterally extending posts 174 which are positioned with one post being in lateral alignment with each of the cylinders 156. The posts are connected to a second annular ring 176 which ring has a central aperture through which wobble stick 170 extends. A foot pedal 178 is connected to the end of the wobble stick and spring 180 is disposed between the foot pedal and annual ring 176 so as to bias the foot pedal away from ring 176. A disc 182 is firmly fixed to wobble stick 170. A microswitch 184 is affixed to each post 174 and extends radially inward toward the wobble stick for actuation by disc 182. Again with reference to FIGS. 5 and 6, it will be seen that conical member 157 upon which cylinders 156 are mounted rises to a point above the cylinders and contains four grooves 186 therein which grooves communicate with depressions 168 in pistons 160 of the cylinders. In this manner, wobble stick 170 may be depressed by the patient toward the front of the cone and will interact with one of the grooves to lead the wobble stick to the depression 168 of one of the cylinders 160 for exercising the patient's extremity. Upon complete depression of one cylinder 160, disc 182 will contact one microswitch 184 which is connected to the post which is disposed laterally of the cylinder being depressed. Upon activation of the microswitch, a signal is sent through leads 186 to circuitry provided for advancing the pointer 188 of patient monitor 114 shown in FIG. 1 to the appropriate indicating mark upon the face of indicating dial 190. The patient is instructed to attempt to rotate pointer 188 in a clockwise manner by sequentially activating microswitches 184 in a clockwise manner through depression of wobble stick 170 into the appropriate cylinders by the injured extremity. In this manner, the patient is provided with regulated exercise to increase the flow of blood in the extremity.

Figure 11:
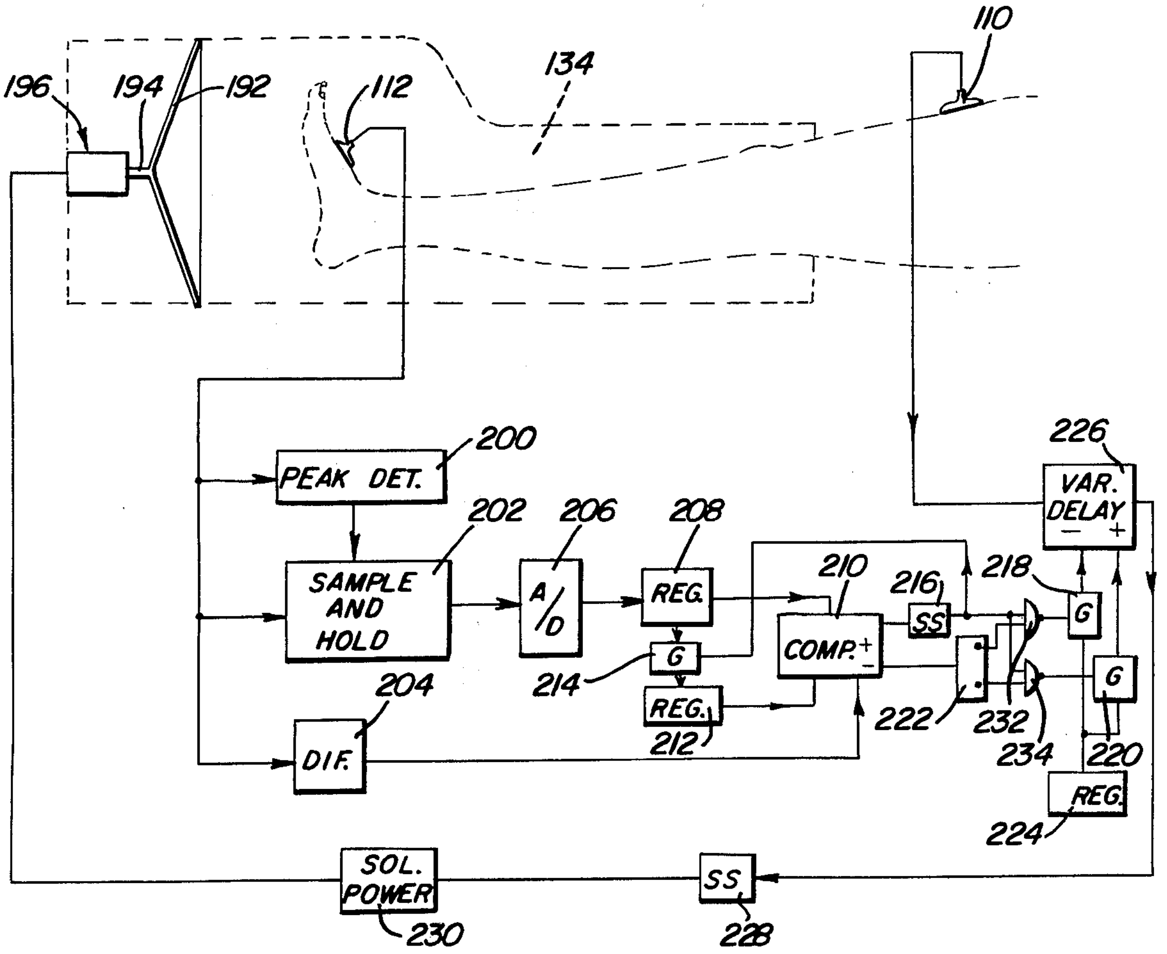
FIG. 11 is a schematic view of circuitry which may be used to synchronize the operation of the pressurizing diaphragm.

An automatic blood circulation assist is provided by pressurization module 106 which may be attached in an airtight manner to the rear of limb casing module 102 or, if the exerciser module is used, to the rear of that module. Again, sealing material is disposed about the edge of the module housing and clasps such as shown at 144 in FIG. 9 may be utilized to secure the attachment arrangement. With reference to FIGS. 1, 4 and 11, the automatic assist apparatus of the present invention will be more clearly set forth. It will be understood that the chamber 134 surrounding the leg 132 is now in airtight condition. In pressurization module 106, a diaphragm 192 is connected to the movable piston 194 of a double acting solenoid 196. It will be clearly understood that upon movement of diaphragm 192 to the position 192' of FIG. 4, the pressure in chamber 134 will be increased while movement of the diaphragm to position 192" will create a partial vacuum in the same chamber. Solenoid 196, of course, creates this diaphragm movement. Movement of the solenoid is controlled by automatic circuitry contained in box 119 of FIG. 1 and shown in detail in FIG. 11. Input to the circuitry is taken from sensors 108, 110 and 112. The outputs from these sensors may be monitored by the patient as shown at 198 in FIG. 1. Control console 119 also may be provided with an oscilloscope to monitor these sensors. It may be noted that by such monitoring, the flow of blood to the patient's body may be envisioned. If a dual trace oscilloscope, as shown, is used, any change in the patient's condition will be immediately apparent to the observer. It will be noted that the largest signal on the oscilloscope would be attributed to the heart beat while the next signal would be attributed to initial extremity surge sensor 110 and the final indication would be due to distal extremity surge sensor 112.

In order to synchronize the action of solenoid 196 with the flow of blood entering the injured extremity, the signal from the sensor 108 or sensor 110 or a combination of the two may be used. The circuit of FIG. 11 shows an exemplary embodiment of circuitry using the signal produced by sensor 110 for such synchronization. With reference to FIG. 11, it will be seen that the sensor 112 is connected to peak detector 200, sample and hold circuit 202, and differentiator 204. Sample and hold 202 is in turn connected to analog to digital converter 206. This analog to digital converter is connected to register 208, the output of which is provided to comparator 210 which compares this output to the output of register 212. Register 212 is connected to register 208 by gate circuit 214. The absolute value of the output of comparator 210 triggers single shot 216, the output of which is gated to either gate 218 or gate 220 based upon the condition of flip-flop 222. Delta register 224 provides a delta signal to variable delay circuit 226. Variable delay circuit 226 receives the output of sensor 110 and transmits it after a time delay to single shot 228 which is in turn connected to solenoid power source 230 which activates solenoid 196.

The operation of the circuit is as follows. A synchronizing pulse from sensor 110 is delayed by the time delay specified by circuit 226 and thereafter transmitted to single shot 228. Single shock 228 provides a signal to solenoid power source 230 whereby circuit 230 activates solenoid 196 in a positive direction on the upward edge of the output of single shot 229 and operates cylinder 196 in the opposite direction upon the downward progressing edge of the pulse from single shot 228. Initially variable time delay 226 is set at zero time delay such that diaphragm 192 will operate simultaneously with the pulse being received from sensor 110. Sensor 112 provides an indication of the surge flow through the body extremity. The amplitude of this signal is detected and stored by detector 200 and sample and hold circuit 202. The output of circuit 202 is converted to a digital signal by analog to digital converter 206 and is stored in register 208. Output of sensor 112 is also differentiated by differentiator 204 which signals comparator 210 to compare the contents of register 208 with the contents of register 212. The absolute value output of comparator 210 is suppled to single shot 216. Single shot 216 provides a pulse if the absolute value of the output of comparator 210 is above a predetermined value. The pulse from single shot 216 activates gate 214 which transfers the contents of register 208 to register 212 in preparation for the next comparison to be made by comparator 210. The output of single shot 216 also is supplied to the AND gates 232 and 234 which receive the complementary outputs of flip-flop 222. Flip-flop 222 is initially set such that the Q output is high. Consequently, if comparator output 210 is positive any output of single shot 216 will be supplied to gate 218 which will increment the time delay by a positive amount set by delta register 224. If the output of comparator 210 is negative, output $\overline{Q}$ will be high thus gating any output of single shot 216 to gate 220 which will decrement the variable delay by an amount equivalent to the contents of delta register 224. In this manner, sequential signals from sensor 112 will be compared in register 210 until the difference between the sequential signals would be too small to activate single shot 216. This will indicate the optimum synchronization for solenoid 196.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A circulation assist device for body extremities comprising:

a casing means for enclosing the body extremity in an airtight environment;

automatic circulation assist means including a pressure producing means connected to said casing means for increasing and decreasing the pressure in said casing means, and a control means for actuating said pressure producing means, said control means including synchronization means for synchronizing the actuation of said pressure producing means to the natural circulation in said extremity; and exercise means for allowing the exercise of said extremity while enclosed in said casing means comprising at least one piston located within the casing and positioned to be depressible by said extremity.

2. The device of claim 1 wherein said automatic circulation assist means further includes monitoring means for monitoring the circulation increase or decrease effected by the control means.

3. The device of claim 1 wherein said control means includes a first circulation sensor means for connection to the body at a position removed from the area and enclosed by said casing means, and a second circulation sensor means for connection to the extremity enclosed by said casing means, whereby said first sensor provides a first pulse for actuating said pressure producing means and said second sensor provides a second pulse to said synchronization means to control the timing of the application of said first pulse to the pressure producing means.

4. A circulation assist device for body extremities comprising:

a casing means for enclosing the body extremity in an airtight environment;

automatic circulation assist means including a pressure producing means connected to said casing means for increasing and decreasing the pressure in said casing means, and a control means for actuating said pressure producing means, said control means including synchronization means for synchronizing the actuation of said pressure producing means to the natural circulation in said extremity; and exercise means for allowing the exercise of said extremity while enclosed in said casing means comprising at least one piston depressible by said extremity; said exercise means including a plurality of pistons which are positioned for individual, sequential depression by said extremity, and indicator means for providing an indication upon the complete depression of each piston.

5. A circulation assist device for body extremities comprising:

a casing means for enclosing the body extremity in an airtight environment;

automatic circulation assist means including a pressure producing means connected to said casing means for increasing and decreasing the pressure in said casing means, and a control means for actuating said pressure producing means, said control means including synchronization means for synchronizing the actuation of said pressure producing means to the natural circulation in said extremity;

exercise means for allowing the exercise of said extremity while enclosed in said casing means comprising at least one piston depressible by said extremity; and pressure applying means connected to said casing means for applying pressure to a wound on said extremity.

6. A circulation assist device for body extremities comprising:

a casing means for enclosing the body extremity in an airtight environment;

automatic circulation assist means including a pressure producing means connected to said casing means for increasing and decreasing the pressure in said casing means, and a control means for actuating said pressure producing means, said control means including synchronization means for synchronizing the actuation of said pressure producing means to the natural circulation in said extremity;

exercise means for allowing the exercise of said extremity while enclosed in said casing means comprising at least one piston depressible by said extremity;

wherein said pressure producing means includes a diaphragm means in operative communication with said casing means for increasing pressure when extended in one direction and decreasing pressure when extended in a second direction;

wherein said control means includes a first circulation sensor means for connection to the body at a position removed from the area enclosed by said casing means, and a second circulation sensor means for connection to the extremity enclosed by said casing means, wherein said first sensor means provides a first pulse for actuation of said solenoid and said second sensor means provides a second pulse to said synchronization means for controlling the timing of the application of the first pulse to the solenoid; and wherein said exercise means includes a plurality of pistons which are positioned for individual sequential depression by said extremity, and indicator means for indicating the completion of the depression of each piston.

7. A device for automatically assisting the circulation of blood in a body extremity comprising:

means for pressurizing said body extremity;

means for sensing the initiation of a blood surge into said extremity;

means for sensing a blood surge at an extreme position on said extremity;

means for actuating said means for pressurizing in response to a signal being received from said means for sensing initiation; and means for delaying the actuation of said means for pressurizing in response to a signal received from said means for sensing a blood surge at an extreme position.

8. A device for automatically assisting the circulation of blood in a body extremity comprising:

means for pressurizing said body extremity;

means for sensing the initiation of a blood surge into said extremity;

means for sensing a blood surge at an extreme position on said extremity;

means for actuating said means for pressurizing in response to a signal being received from said means for sensing initiation;

means for delaying the actuation of said means for pressurizing in response to a signal received from said means for sensing a blood surge at an extreme position;

and further in combination with an exercise means for promoting blood circulation by stimulation through exercise comprising;

an hydraulic reservoir;

a plurality of hydraulic cylinders in communication with said reservoir, each cylinder having a spring biased piston included therein;

means for depressing each of said pistons one at a time; and means for providing an indication of depression of each piston.

9. The device of claim 8 wherein said exercise means is in modular form and includes latch means for easily attaching and detaching the exercise means to the automatic circulation assist device.

10. The device of claim 8 wherein said means for providing an indication includes a dial indicator having one marking corresponding to each piston and a pointer which points to the marking corresponding to the piston the depression of which has just been completed.

* * * * *